United States Patent
Strähle

[11] Patent Number: 5,825,534
[45] Date of Patent: Oct. 20, 1998

[54] STEREOENDOSCOPE HAVING A FOLDED SIGHT LINE

[75] Inventor: Fritz Strähle, Heubach, Germany

[73] Assignee: Carl-Zeiss-Stiftung, Heidenheim, Germany

[21] Appl. No.: 524,536

[22] Filed: Sep. 7, 1995

Related U.S. Application Data

[63] Continuation-in-part of Ser. No. 510,697, Aug. 3, 1995, Pat. No. 5,612,816, which is a continuation of Ser. No. 100,276, Aug. 2, 1993, abandoned, and Ser. No. 875,634, Apr. 28, 1992, Pat. No. 5,321,447.

[30] Foreign Application Priority Data

Sep. 8, 1994 [DE] Germany .......................... 44 31 968.1

[51] Int. Cl.⁶ .................................................. G02B 21/22
[52] U.S. Cl. ........................... 359/376; 359/377; 359/381; 359/831
[58] Field of Search ...................... 359/368, 376, 359/378, 433–435, 362; 385/32, 36; 600/101–116, 170–172, 166; 348/45, 65, 72

[56] References Cited

U.S. PATENT DOCUMENTS

| | | | |
|---|---|---|---|
| 4,061,135 | 12/1977 | Widran et al. ........................... | 600/111 |
| 4,138,192 | 2/1979 | Yamasita ................................. | 359/726 |
| 4,140,364 | 2/1979 | Yamashita et al. ..................... | 359/367 |
| 4,398,811 | 8/1983 | Nishioka et al. ....................... | 600/171 |
| 4,655,557 | 4/1987 | Takahashi ............................... | 359/735 |
| 4,815,833 | 3/1989 | Zobel et al. ............................ | 359/726 |
| 4,838,247 | 6/1989 | Forkner .................................. | 600/173 |
| 5,295,477 | 3/1994 | Janfaza .................................. | 359/368 |
| 5,341,240 | 8/1994 | Broome .................................. | 359/435 |
| 5,377,047 | 12/1994 | Broome et al. ........................ | 359/362 |
| 5,496,261 | 3/1996 | Sander .................................. | 359/379 |

FOREIGN PATENT DOCUMENTS

| | | |
|---|---|---|
| 0571725 | 12/1993 | European Pat. Off. . |
| 937193 | 12/1955 | Germany . |
| 2919678 | 11/1980 | Germany ............................. 359/377 |
| 3537155 | 4/1986 | Germany . |
| 44 05 102 | 8/1994 | Germany . |

Primary Examiner—Thong Nguyen
Attorney, Agent, or Firm—Walter Ottesen

[57] ABSTRACT

The invention relates to a stereoendoscope having a sight line folded relative to the tube axis. The endoscope includes a distal front optic having a deflecting prism 4b. The deflecting prism 4b is mounted between a component 4a having a negative refractive power and a proximal component 4c having a positive refractive power. The inlet pupils 11 of the viewing component are imaged demagnified in the reflecting prism 4b by field optics (7, 7', 13) and transmitting optics (8, 8', 14). In this way, the beam can be guided free of vignetting without field cropping for both stereo channels through the endoscope tube and through the reflecting prism 4b even for a large object field angles and without image cropping. The endoscope tube 2 and the viewing component 1 are rotatable with respect to each other about the optical axis 12 within the endoscope tube 2 so that the line of sight can be changed for a viewing component fixed in space. The stereo basis remains for a rotation of the endoscope tube 2 fixed in space.

11 Claims, 3 Drawing Sheets

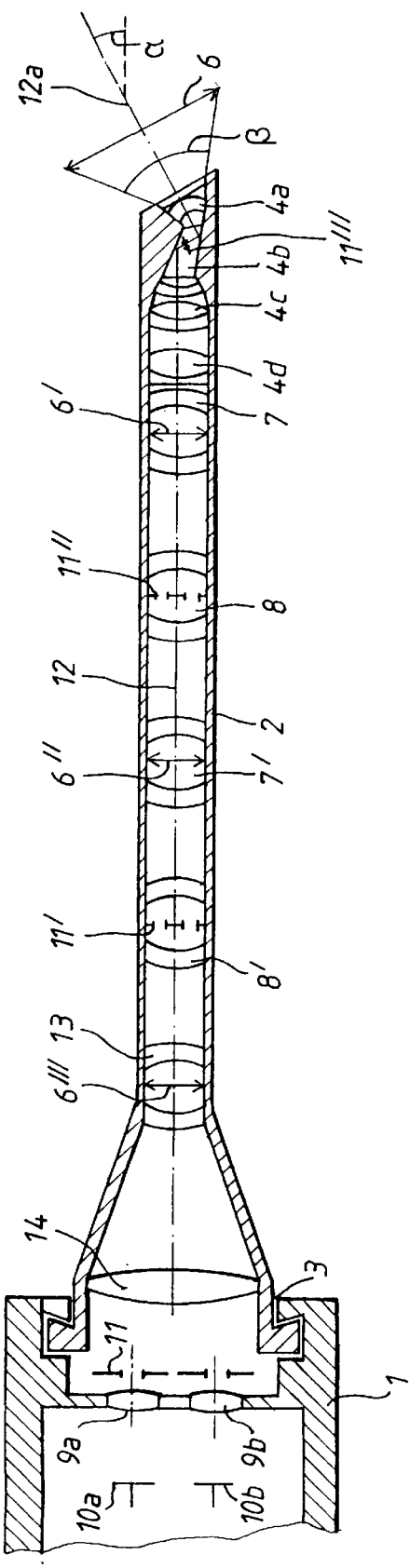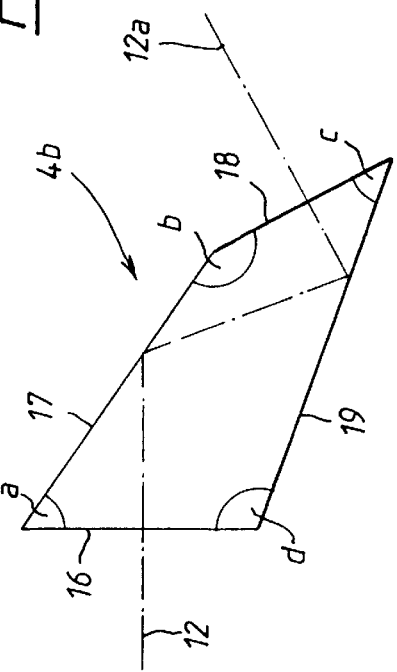

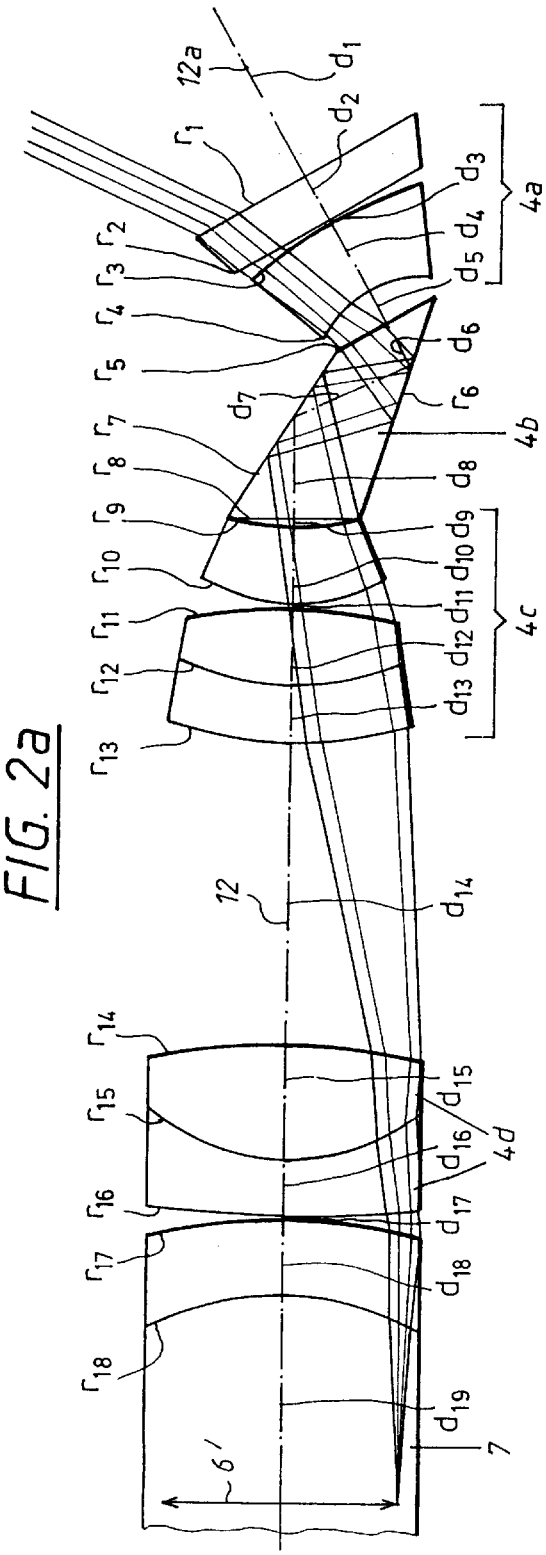
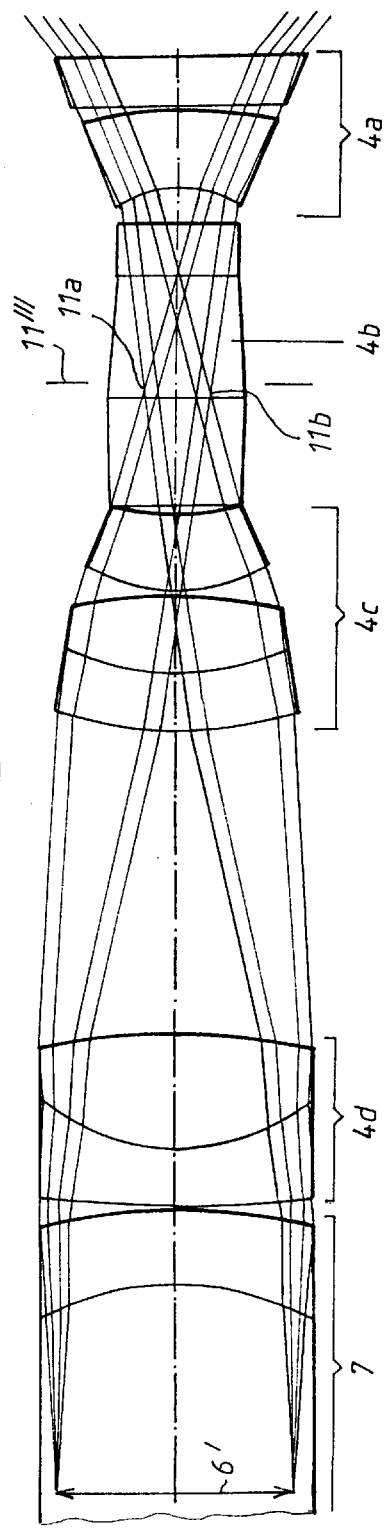
FIG. 2a
FIG. 2b

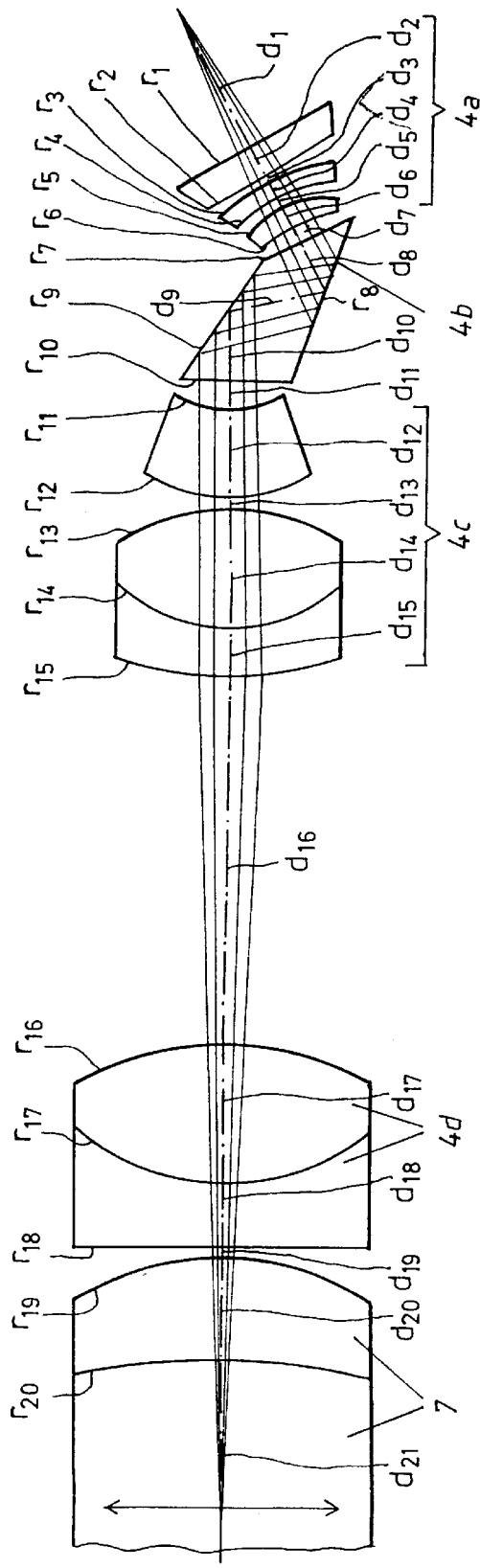
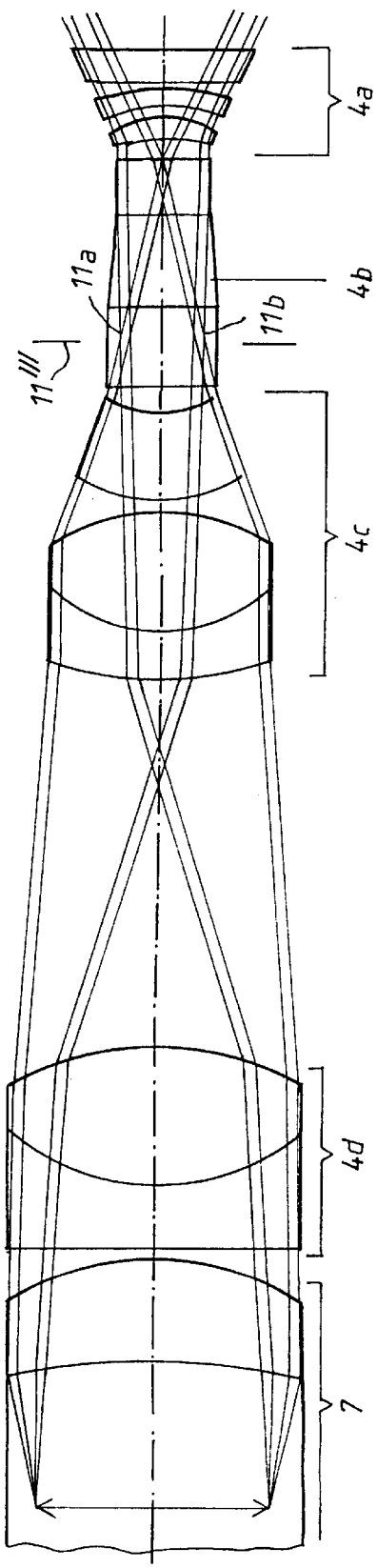
FIG.3a
FIG.3b ial applications P 42 25 507.4 and P 43 01 466.6 which, in turn, is a continuation of U.S. patent application Ser. No. 08/100,276, filed Aug. 2, 1993 (now abandoned) as well as a continuation-in-part application of U.S. patent application Ser. No. 07/875,634, filed Apr. 28, 1992 (now U.S. Pat. No. 5,321,447) and claiming priority of German patent application P 41 14 646.

BACKGROUND OF THE INVENTION

The different areas of application of endoscopy include laparoscopy and arthroscopy. In these different areas of application, endoscopes having a straight sight line are required as are endoscopes having a sight line which is folded, for example, by 30°. The folding of the sight line fulfills primarily two objectives: on the one hand, the useable viewing field angle is increased by twice the folding angle in that the endoscope is rotated by 180° about its axis. On the other hand, areas of the region of surgery, which would otherwise be difficult to access and difficult to view, are brought easily into the center of the viewing field. This then provides a decisive convenience in many practical areas of application because the simultaneous viewing of an adequately large background region is a necessary precondition for the surgeon for conducting reliable surgery.

U.S. Pat. No. 4,061,135 discloses an endoscope wherein a mirror is mounted forward of the distal front optic. The mirror is inclined with respect to the axis of the endoscope tube. Endoscopes usually have a large viewing field of 50° and more. However, for this reason, such a distal deflecting mirror must be greater in its dimensions than the diameter of the optic tube if the mirror should not lead to a cropping of the image field.

Furthermore, monoendoscopes having a folded sight line are known wherein the distal front optic includes one or more deflecting prisms folding the optical axis. Examples of such monoendoscopes are disclosed in U.S. Pat. Nos. 4,138, 192; 4,815,833 and 4,655,557 as well as German patent publications 937,193; 2,430,148; 3,537,155 and 2,458,306. European patent publication 0,571,725 also discloses such a monoendoscope. In a first set of the solutions for monoendoscopes known in the state of the art, for example, U.S. Pat. No. 4,655,557, one of the reflective surfaces is aligned parallelly to the optical axis of the optic tube. The endoscope tube must have a significantly greater diameter than the optic tube so that such a planar reflecting surface can be mounted in the endoscope tube. This is, however, unsatisfactory for stereoendoscopes wherein the light-conductance value for each stereo channel is a maximum of one quarter of the light-conductance value of a monoendoscope having the same optic diameter.

In a second set of solutions known for monoendoscopes, the reflecting surfaces of the prism are inclined to the axis of the optical tube as disclosed, for example, in U.S. Pat. No. 4,138,192. In this way, the optic tube can fill out almost the entire endoscope tube. However, the entire guided beam within the reflecting prisms has only a minute expansion perpendicular to the optical axis in comparison to the diameter of the optic tube. Furthermore, conventional monoendoscopes, which are standardized to an outer diameter of 10 mm, have a light-conductance value of less than 0.2; whereas, a light-conductance value of 0.27 is necessary for a good stereo image. For this reason, these solutions also appear to be unsuitable for stereoendoscopes.

SUMMARY OF THE INVENTION

It is an object of the invention to provide a stereoendoscope with a folded sight line wherein no cropping of the viewing field takes place even for large viewing-field angles, for example, viewing field angles of greater than 60°.

The stereoendoscope of the invention includes: an endoscope tube defining a tube axis; a transmitting optic assembly mounted in the endoscope tube and defining a first optical axis extending parallel to or being coaxial with the tube axis; a front optic assembly having a proximal end adjacent the transmitting optic assembly and a distal end facing away from the transmitting optic assembly; the front optic assembly including a prism mounted between the proximal and distal ends and defining a second optical axis at the proximal end aligned coaxially with the first optical axis; and, the front optic assembly further defining a third optical axis at the distal end aligned so as to define an angle with the first optical axis unequal to 0° and 180°.

The stereoendoscope of the invention includes a transmitting optic having an optical axis parallel or coaxial to the axis of the endoscope tube. In addition, the stereoendoscope includes a front optic having a prism and the proximal optical axis of the front optic is coaxial to the optical axis of the transmitting optic and the distal optical axis extends at an angle to the optical axis of the transmitting optic. This angle is an angle other than 0° or 180°.

Cropping of the image field can be avoided because the deflection takes place in a prism within the front optic. In this way, it is especially advantageous when the front optic has a distal component having a negative refractive power and a proximal component having a positive refractive power and the prism is mounted between the two components. The light of a large object field or viewing field can be coupled in at the light in-couple surface of the reflecting prism because the distal component has the negative refractive power. Because of the component having a positive refractive power mounted rearward of the reflecting prism, the beam emanating from the prism can be expanded in such a manner that each of the two stereoscopic partial images assumes almost the entire free diameter of the transmitting optic or of the optic tube.

It is especially useful to configure the distal light-entry surface of the prism to be smaller than the proximal light-exit surface thereof in order to guide both stereo partial beam paths for each image point or object point without vignetting and without cropping the viewing field. The two entry pupils of the stereoscopic viewing system are spaced from each other in correspondence to the stereo basis. The two entry pupils should then be imaged demagnified in the prism. The stereo basis is imaged demagnified at the same imaging scale as the entry pupils.

In order to make all-around viewing possible, the endoscope tube and the viewing system should be rotatable relative to each other about the optical axis of the transmitting optic. Viewing along different lines of sight is then possible for a fixed spatial orientation of the stereo basis of the viewing system. The reflecting prism should have two reflecting surfaces so that the image rotation takes place unreversed to the rotation of the endoscope tube.

The angle between the proximal and the distal optical axis of the front optic should be 30° and the distal viewing field angle should be at least 60° so that a total object field angle of 120° is provided with an unchanged endoscope position. For a viewing field angle and a deflecting angle of these magnitudes, the reflecting prism should be made of a material having a refractive index of greater than 2.0 and should be separated by an air gap from the distal component and be separated by an air gap from the proximal component. Furthermore, the angle between the proximal light-exit surface and the second reflection surface of the reflecting prism should be greater than 56°.

For a special advantageous embodiment, the front optic has a single reflecting prism whose light-entry surface is aligned perpendicularly to the distal optical axis and whose light-exit surface is aligned perpendicularly to the proximal optical axis of the front optic. In this way, no additional correcting prisms for avoiding astigmatism are required.

BRIEF DESCRIPTION OF THE DRAWINGS

The invention will now be described with reference to the drawings wherein:

FIG. 1 is a schematic section view of a stereoendoscope according to a first embodiment of the invention;

FIG. 2a is a section view through the lenses of the front optic of the stereoendoscope of FIG. 1;

FIG. 2b is a section view through the lenses of the front group of FIG. 2a in a view extending along the optical axis;

FIG. 3a is a section view of an alternate embodiment for the front optic;

FIG. 3b is a section view of the front optic of FIG. 3a extending along the optical axis; and, FIG. 4 is a section view through the reflecting prism of the front optics of the FIGS. 2 and 3.

DESCRIPTION OF THE PREFERRED EMBODIMENTS OF THE INVENTION

The stereoendoscope of FIG. 1 essentially includes a viewing system or component 1 and a thin endoscope tube 2 attached thereto. The distal front optic (4a to 4d) and the transmitting optic (8, 8', 14) with field optics (7, 7', 13) are all mounted within the endoscope tube 2. The front optic (4a to 4d) includes a single reflecting prism 4b wherein the beam path is reflected twice so that the optical entry axis 12a is deflected by an angle α of 30° to the optical axis 12 of the transmitting optic within the endoscope tube. The distal viewing field angle β is 70°.

The front optic (4a to 4d) includes essentially three components, namely: the distal component 4a having a negative refractive power, the reflecting prism 4b and one or two components (4c, 4d) having positive refractive powers. The front optic (4a to 4d) images the object field 6 in the intermediate image 6'. This intermediate image 6' is intermediately imaged within the endoscope tube 2 twice in the intermediate images 6" and 6'" by the transmitting optic (8, 8'). The proximal real intermediate image 6'" is imaged at infinity by an objective 14. Two tube lenses (9a, 9b) are mounted at a spacing corresponding to the stereo basis within the viewing system 1. The tube lenses (9a, 9b) generate respective stereo partial images on corresponding camera chips (10a, 10b).

The objective 14, field optic 13 and the proximal component of a transmitting optic 8' within the endoscope conjointly define an inverted telescope by means of which the entry pupils 11 are imaged demagnified in the endoscope tube. The entry pupils 11 are spaced from each other in correspondence to the stereo basis. Further field optics (7, 7') and transmitting optics (8, 8') image the pupil image 11' as well as the intermediate image 6' several times within the endoscope tube at a scale of 1:1.

The entire optic proximal to the front optic (4a to 4d) is configured as shown for the endoscope disclosed in a U.S. patent application Ser. No. 08/510,697, filed on Aug. 3, 1995 which is a continuation application of application Ser. No. 08/100,276, filed Aug. 2, 1993, as well as a continuation-in-part application of application Ser. No. 07/875,634, filed Apr. 28, 1992 (now U.S. Pat. No. 5,321,447) and is incorporated herein by reference. In correspondence to this teaching, a common optic is provided within the endoscope tube for the two stereo channels. The stereo basis as well as the entry pupils of the viewing system are imaged by the inverted telescope (13, 14) in the same scale in the endoscope tube. The United States patent application filed on Aug. 3, 1995 and noted above can be referred to for the exact construction data for the optic proximal to the front optic (4a to 4d).

In contrast to the arrangement of said United States patent application filed on Aug. 3, 1995, the pupil intermediate image 11" is, however, imaged demagnified by the field optic 7 and the proximal components (4c, 4d) of the front optic in the reflecting prism 4b (pupil image 11'"). This demagnified image of the pupils as well as of the stereo basis in the reflecting prism 4b makes it possible to guide the beam in the entire system free of vignetting and without the viewing field being cropped by the reflecting prism 4b.

To change the sight line, the endoscope tube 2 is rotatable at the interface 3 about the optical axis 12 of the transmitting optic (8, 8', 14). The orientation of the stereo basis is maintained in space because the orientation of the viewing part 1 in space remains unchanged. However, since the orientation of the pupil image 11'" is changed within the reflecting prism 4b, the reflecting prism 4b is so configured that no vignetting and no cropping of the viewing field occurs for a rotation about the optical axis 12. Since the beam path within the reflecting prism is twice reflected, the image is correct laterally as well as with respect to elevation and a stereoscopically correct depth impression is ensured because of the pupil imaging.

The guidance for the stereoscopic partial beam paths within the front optic (4a to 4d) is shown in the lens section views of FIGS. 2a and 2b. In FIG. 2a, and for the sake of clarity, the stereo beams are shown only for a single object point and, in FIG. 2b, the stereo beams for two object points positioned at opposite edges of the viewing field are shown. As can be seen especially from FIG. 2b, the image 6' for each object point is generated by two stereo partial beams. These stereo partial beams are separated from each other within the reflecting prism 4b for stereo beams of the same point of the object; however, for stereo partial beams of different object points belonging to the same stereo channel, common pupils (11a and 11b) are passed through. As shown further in FIG. 2b, the two intermediate images 6' are superposed completely for both stereo channels. This results from the common transmitting optic within the endoscope and leads to an increased light conductance.

The specific construction data of the front optic of FIGS. 2a and 2b are presented in Table I. The surfaces and the thicknesses or distances along the optical axis of the components are numbered continuously beginning at the object field (object field or working distance $d_1$). The spacings and thicknesses are measured along the optical axis between the intersect points of the optical axis with neighboring surfaces. The surface radii of curvature are given as radii. The materials used are available in the marketplace and are made by the Schott Company of Mainz, Germany, under the indicated product designations.

As shown clearly in FIGS. 2a and 2b, the reflecting prism 4b has two reflecting surfaces inclined to the optical axis of the proximal components (4c, 4d) and has light-entry and light-exit surfaces aligned perpendicularly to the particular optical axes (12, 12a). Furthermore, the light-entry surface is smaller than the light-exit surface and the prism 4b is separated from the distal component 4a by an air spacing $d_5$ and from the next adjacent proximal component 4c by an air spacing $d_9$. With these measures, the stereo partial beams can be guided without vignetting through the prism 4b even for a large viewing field of 70°.

The embodiment for the front optic in accordance with FIGS. 3a and 3b differs from the embodiment of FIGS. 2a and 2b essentially in that the distal component 4a has two elements having negative refractive power. The construction data of these two embodiments are delineated in Table II. In contrast to the embodiment of Table I wherein the object field diameter is 88.6 mm, the object field diameter of 89 mm in the embodiment of Table II is slightly greater for the same intermediate image size of 6.2 mm. With respect to the radii $r_i$ and spacings or thicknesses $d_i$ presented in Table II, the descriptions given above for Table I apply. In the embodiment of FIGS. 3a and 3b, the entry surface of prism 4b is separated from component 4a by the air spacing $d_7$ and the exit surface of the prism is separated from component 4c by the air spacing $d_{11}$.

In the section view of FIG. 4, the reflecting prism 4b is shown enlarged and is identical in the embodiments of Tables I and II. The reflecting prism 4b has a light-entry surface 18, two reflecting surfaces (17, 19) and a light-exit surface 16. The angle (a) between the light-exit surface 16 and the second reflecting surface 17 is 56.5°. The angle (b) between the light-entry surface 18 and the second reflecting surface 17 is 153.5° and the angle (c) between the light-entry surface 18 and the first reflecting surface 19 is 41.5° and the angle (d) between the first reflecting surface 19 and the light-exit surface 16 is 108.5°. The light-entry surface 18 is perpendicular to the distal optical axis 12a and has a cross section length of 2.975 mm and the light-exit surface 16 perpendicular to the proximal optical axis 12 has a cross section length of 3.5 mm. The light-entry surface 18 is therefore smaller than the light-exit surface 16. This is necessary so that the guidance of the beam within the prism 4b for both stereo channels can be free of vignetting and can take place without field cropping even for a large field angle of 70°.

The light-entry surface 18 and the light-exit surface 16 are perpendicular to corresponding ones of the optical axes (12, 12a). For this reason, the occurrence of astigmatism is avoided even without a correcting prism. The prism 4b is made of a high-refracting material having a refractive index n=2.03 and is separated from the neighboring components 4a and 4c by respective air spacings so that a strong refraction occurs when entering and exiting the prism.

For the embodiments of Tables I and II, a light-conductance value of 0.31 results for a maximum clear optical diameter of 7.3 mm. The light-conductance value is calculated for a beam having a diameter which corresponds to the sum of the stereo basis and the stereo pupil and therefore corresponds to a monoendoscopic application. This light-conductance value is greater than the value of 0.27 required for a good stereoendoscopic image so that a good imaging quality is ensured even for a maximum outer diameter of the endoscope tube 2 of 10 mm distally of the field optic 13.

With respect to FIG. 1, the invention was explained in the context of a video endoscope. The invention is, however, also useable for endoscopes providing ocular viewing wherein the camera chips (10a, 10b) are substituted by a telescope comprising a stereo tube and two oculars.

It is understood that the foregoing description is that of the preferred embodiments of the invention and that various changes and modifications may be made thereto without departing from the spirit and scope of the invention as defined in the appended claims.

TABLE I

| Component | Radius $r_i$ (mm) | Thickness or Spacing $d_i$ (mm) | Medium |
|---|---|---|---|
|  |  | $d_1$ = 60.00 | Air |
|  | $r_1 = \infty$ |  |  |
|  |  | $d_2$ = 1.300 | ZKN7 |
|  | $r_2 = \infty$ |  |  |
| 4a |  | $d_3$ = 0.100 | Air |
|  | $r_3$ = 17.0310 |  |  |
|  |  | $d_4$ = 2.000 | LASFN30 |
|  | $r_4$ = 2.85920 |  |  |
|  |  | $d_5$ = 1.000 | Air |
|  | $r_5 = \infty$ |  |  |
|  |  | $d_6$ = 1.316 | LASF35 |
|  | $r_6 = \infty$ |  |  |
| 4b |  | $d_7$ = 3.336 | LASF35 |
|  | $r_7 = \infty$ |  |  |
|  |  | $d_8$ = 2.644 | LASF35 |
|  | $r_8 = \infty$ |  |  |
|  |  | $d_9$ = 0.300 | Air |
|  | $r_9$ = −7.82980 |  |  |
|  |  | $d_{10}$ = 2.000 | SK2 |
|  | $r_{10}$ = −5.08450 |  |  |
| 4c |  | $d_{11}$ = 0.100 | Air |
|  | $r_{11}$ = 14.1250 |  |  |
|  |  | $d_{12}$ = 2.000 | SK5 |
|  | $r_{12}$ = −7.39180 |  |  |
|  |  | $d_{13}$ = 1.500 | SF10 |
|  | $r_{13}$ = −11.3010 |  |  |
|  |  | $d_{14}$ = 8.326 | Air |
|  | $r_{14}$ = 18.4340 |  |  |
| 4d |  | $d_{15}$ = 3.000 | SSKN8 |
|  | $r_{15}$ = −5.54310 |  |  |
|  |  | $d_{16}$ = 1.500 | SFL56 |
|  | $r_{16}$ = −54.6390 |  |  |
|  |  | $d_{17}$ = 0.100 | Air |
|  | $r_{17}$ = 14.5380 |  |  |
| 7 |  | $d_{18}$ = 2.000 | SFL56 |
|  | $r_{18}$ = 7.71790 |  |  |
|  |  | $d_{19}$ = 5.500 | F5 |

Object Field Diameter: 88.6 mm
Maximum Clear Optic Diameter: 7.3 mm

TABLE II

| Component | Radius $r_i$ (mm) | Thickness or Spacing $d_i$ (mm) | Medium |
|---|---|---|---|
|  |  | $d_1$ = 60.16 | Air |
|  | $r_1 = \infty$ |  |  |
|  |  | $d_2$ = 1.300 | ZKN7 |
|  | $r_2 = \infty$ |  |  |
|  |  | $d_3$ = 0.100 | Air |
|  | $r_3$ = 10.000 |  |  |
| 4a |  | $d_4$ = 1.200 | LASFN30 |
|  | $r_4$ = 3.11710 |  |  |
|  |  | $d_5$ = 0.600 | Air |
|  | $r_5$ = 7.94330 |  |  |
|  |  | $d_6$ = 1.200 | LASFN30 |
|  | $r_6$ = 3.34970 |  |  |
|  |  | $d_7$ = 1.000 | Air |
|  | $r_7 = \infty$ |  |  |
|  |  | $d_8$ = 1.316 | LASF35 |
|  | $r_8 = \infty$ |  |  |
| 4b |  | $d_9$ = 3.336 | LASF35 |
|  | $r_9 = \infty$ |  |  |

TABLE II-continued

| Component | Radius $r_i$ (mm) | Thickness or Spacing $d_i$ (mm) | Medium |
|---|---|---|---|
| | | $d_{10}$ = 2.644 | LASF35 |
| | $r_{10}$ = ∞ | | |
| | | $d_{11}$ = 0.400 | Air |
| | $r_{11}$ = −7.60760 | | |
| | | $d_{12}$ = 2.000 | SSKN8 |
| | $r_{12}$ = −4.94030 | | |
| | | $d_{13}$ = 0.100 | Air |
| 4c | $r_{13}$ = 17.2780 | | |
| | | $d_{14}$ = 2.000 | SK5 |
| | $r_{14}$ = −6.21940 | | |
| | | $d_{15}$ = 1.500 | SF10 |
| | $r_{15}$ = −10.7460 | | |
| | | $d_{16}$ = 13.50 | Air |
| | $r_{16}$ = 25.3000 | | |
| | | $d_{17}$ = 3.000 | SSKN8 |
| 4d | $r_{17}$ = −5.54310 | | |
| | | $d_{18}$ = 1.500 | SFL56 |
| | $r_{18}$ = ∞ | | |
| | | $d_{19}$ = 0.100 | Air |
| | $r_{19}$ = 11.1400 | | |
| 7 | | $d_{20}$ = 2.000 | SFL56 |
| | $r_{20}$ = 7.71790 | | |
| | | $d_{21}$ = 5.500 | F5 |

Object Field Diameter: 89 mm
Maximum Clear Optic Diameter: 7.3 mm

What is claimed is:

1. A stereoendoscope providing a viewing field to an observer, the stereoendoscope comprising;
an endoscope tube;
a transmitting optic assembly mounted in said endoscope tube and defining a first optical axis;
a front optic assembly having a proximal end adjacent said transmitting optic assembly and a distal end facing away from said transmitting optic assembly;
said front optic assembly defining a second optical axis at said distal end and including a prism mounted between said proximal and distal ends;
said proximal end being aligned with said first optical axis;
said second optical axis at said distal end being aligned so as to define an angle with said first optical axis unequal to 0° or 18°;
said transmitting optic assembly having an end facing away from said front optic assembly;
a viewing system disposed on said first optical axis so as to be adjacent said end of said transmitting optic assembly;
said viewing system having two pupils spaced from each other; and,
said transmitting optic assembly including field optics for imaging said two pupils demagnified into said prism so that a beam guided through said stereoendoscope is vignette free and said viewing field is uncropped by said prism.

2. The stereoendoscope of claim 1, said front optic assembly including:
a proximal lens component defining said proximal end and said proximal lens component having a positive refractive power; and, a distal lens component defining said distal end and said distal lens component having a negative refractive power; and,
said prism being mounted between said proximal and distal lens components.

3. The stereoendoscope of claim 2, said prism having a distal light entry surface and a proximal light exit surface; said prism also having four optically effective surfaces, two of said optically effective surfaces being said entry and exit surfaces and the remaining ones of said optically effective surfaces being first and second reflecting surfaces between said entry and exit surfaces for reflecting light entering via said entry surface and travelling to said exit surface; and, said distal light entry surface having an area less than the area of said proximal light exit surface.

4. The stereoendoscope of claim 3, wherein the images of said pupils in said prism are apart from each other at a spacing demagnified at the same scale as said images of said pupils.

5. The stereoendoscope of claim 4, said viewing system and said endoscope tube conjointly defining an interface which permits said viewing system and said endoscope tube to be rotated relative to each other about said first optical axis.

6. The stereoendoscope of claim 3, wherein: said first optical axis and said second optical axis conjointly define an angle ($\alpha$) equal to at least 30°; and, said front optic assembly define a distal image angle ($\beta$) equal to at least 60°.

7. The stereoendoscope of claim 6, said proximal light exit surface and said second reflecting surface conjointly defining an angle greater than 56°.

8. The stereoendoscope of claim 7, said endoscope tube defining a tube axis and said first and second reflecting surfaces being inclined to said tube axis.

9. The stereoendoscope of claim 3, said prism being the only prism of said front optic assembly; said light entry surface being perpendicular to said second optical axis and said light exit surface being perpendicular to said first optical axis.

10. The stereoendoscope of claim 2, said prism being made of a material having a refractive index greater than 2.00; said prism and said proximal lens component conjointly defining a first air spacing therebetween; and, said prism and said distal lens component conjointly defining a second air spacing therebetween.

11. The stereoendoscope of claim 1, said endoscope tube defining a tube axis and said first optical axis being coaxial with said tube axis.

* * * * *

UNITED STATES PATENT AND TRADEMARK OFFICE
CERTIFICATE OF CORRECTION

PATENT NO. : 5,825,534
DATED : October 20, 1998
INVENTOR(S) : Fritz Straehle

It is certified that error appears in the above-identified patent and that said Letters Patent is hereby corrected as shown below:

Column 7,
Line 29: delete "comprising;" and substitute -- comprising: -- therefor.
Line 43: delete "18°" and substitute -- 180° -- therefor.

Signed and Sealed this

Eighteenth Day of September, 2001

Attest:

NICHOLAS P. GODICI
Attesting Officer
Acting Director of the United States Patent and Trademark Office